United States Patent [19]
Krebs et al.

[11] 3,930,497
[45] Jan. 6, 1976

[54] SURGICAL DRAPE AND SYSTEM INCORPORATING IT

[75] Inventors: Kay E. Krebs; Marion T. Arps, both of Neenah, Wis.

[73] Assignee: Kimberly-Clark Corporation, Neenah, Wis.

[22] Filed: Dec. 5, 1974

[21] Appl. No.: 529,633

[52] U.S. Cl............................................ 128/132 D
[51] Int. Cl.$^2$........................................ A61F 13/00
[58] Field of Search............... 128/132 D, 292, 296

[56] References Cited
UNITED STATES PATENTS

| | | | |
|---|---|---|---|
| 3,030,957 | 4/1962 | Melges............................ | 128/132 D |
| 3,263,680 | 8/1966 | Morgan............................ | 128/132 D |
| 3,669,106 | 6/1972 | Schrading et al............... | 128/132 D |
| 3,791,381 | 2/1974 | Krzewinski...................... | 128/132 D |
| 3,835,851 | 9/1974 | Villari............................. | 128/132 D |

*Primary Examiner*—L. W. Trapp
*Attorney, Agent, or Firm*—Daniel J. Hanlon, Jr.; William D. Herrick; Raymond J. Miller

[57] ABSTRACT

A drape for use in surgical procedures having a base sheet of a liquid-repellent material and including a generally U-shaped fenestration with a layer of adhesive surrounding the fenestration and providing for varying the dimensions of the fenestration. The adhesive is protected by a plurality of cover strips which permit the drape to be applied in a folded condition to the patient and unfolded with reduced danger of contamination. In a preferred embodiment the drape also includes a foam-film laminate layer on the top surface thereof around the fenestration for placement of instruments, increased protection against liquid strike-through, reduced glare, and controlled absorbency. In use, the drape of the invention may be combined with other drapes, and an application is described including a stocking and a bar sheet for complete protection in complicated procedures such as knee or hip surgery. An improved method of folding the drape of the invention for increased safety and convenience is also described.

10 Claims, 9 Drawing Figures

SURGICAL DRAPE AND SYSTEM INCORPORATING IT

BACKGROUND OF THE INVENTION

1. Field of the Invention

The present invention relates to surgical drapes especially adapted for use in highly complex surgical procedures such as hip, knee or leg surgery. In particular, it is directed to such surgical drapes including a generally U-shaped fenestration and adhesive means for attachment to the patient. Further, the invention is concerned with methods for folding such drapes so as to provide a compact package that may be quickly unfolded and applied with reduced danger of contamination.

2. Description of the Prior Art

Historically, the preparation of a patient for surgery has involved covering all exposed portions except the area of the incision with rectangular sheets of muslin. Disadvantages of this procedure include the tendency of muslin to lint and the accompanying danger of lint entering the incision, the ability of most liquids to wet through muslin thus breaking the sterile barrier, and the high cost of the laundering/reuse cycle.

With the advent of nonwovens, surgical drapes designed for single use have been produced at a cost which makes their use practical. Further, disposable drapes can be manufactured from relatively non-linting, liquid-repellent materials that reduce the risk to the patient. In addition to the convenience of disposability, some of these drapes have been provided with adhesive attachment means to resist displacement of the drape once it is firmly fixed in position. A wide variety of disposable surgical drapes have been produced for varying surgical procedures including non-fenestrated drapes, fenestrated drapes, and split sheets or sheets having a U-shaped fenestration in one end. Examples of such are included in U.S. Pat. NO. 3,494,356 to Melges issued Feb. 10, 1970; U.S. Pat. 3,669,106 to Schrading and Winters issued June 13, 1972; U.S. Pat. No. 3,693,618 to Madden issued Sept. 26, 1972; and U.S. Pat. No. 3,668,050 to Donnelly issued June 6, 1972.

While disposable surgical drapes have met with success in solving many of the problems relating to the use of muslin sheets, in more complicated limb surgery disposable drapes heretofore have not been entirely satisfactory. For example, in hip surgery, an operation being performed in ever-increasing numbers, it is necessary to cover the patient completely including legs and other body members, except in the specific area of the incision. This surgical procedure often takes a number of hours and may involve movement of the patient's leg or legs. Thus, the demands placed on the surgical drape to completely seal off the area of the incision in a manner that will last for hours and withstand physical movement are most difficult to meet. Prior art methods such as those described in the patents to Melges and Madden mentioned above involving the use of ties and/or multiple adhesive strips have proven to be largely unsatisfactory when applied to long, complicated surgical procedures. Even the split sheet as illustrated, for example, in FIG. 4 of the Schrading and Winters patent recited above has not proven readily adaptable to such procedures because of the lack of a complete seal around the fenestration and the difficulty in applying the drape by means of two adhesive strips while simultaneously unfolding it over a large area without contamination.

SUMMARY OF THE INVENTION

The present invention provides a disposable surgical drape that can be used for complicated limb surgery without the drawbacks of the surgical drapes of the prior art as discussed above. The drape of the present invention includes a base sheet of liquid repellent material having a U-shaped fenestration with a layer of normally tacky pressure-sensitive adhesive surrounding the closed end and at least a portion of the sides of the fenestration. Prior to use, the adhesive is protected by separate release sheets for the adhesive around the closed end of the fenestration and one or more release sheets for the remainder of the adhesive. The drape is folded in a manner that provides for the adhesive layer at the closed end with its release sheet to be exposed so that this adhesive area may be placed in contact with the patient prior to unfolding the drape. After this attachment is made, the drape may be unfolded in a convenient and safe manner in position over the patient. Subsequent to removal of the remaining release sheet or sheets, the tails formed by the fenestration may be placed in position so as to produce a fenestration in the desired area and of a size convenient for the particular surgery to be performed. Thus, the improved drape of the present invention provides an extremely convenient and versatile cover that results in a substantially complete seal around the operative site for increased protection against contamination.

Additional embodiments include the combination of this drape with other drapes such as leggings and bar sheets, for example, to form a system designed for a particular operative procedure. Further, it is preferred to provide the drape of the invention with a foam-film laminate on its upper surface to provide protection against liquid strike-through and a non-glare, absorbent, slip-resistant surface to receive instruments or the like in the immediate area of the incision.

DESCRIPTION OF THE PREFERRED EMBODIMENTS

While the invention will be described in connection with preferred embodiments, it will be understood that it is not intended to limit the invention to those embodiments. On the contrary, it is intended to cover all alternatives, modifications, and equivalents as may be included within the spirit and scope of the invention as defined by the appended claims.

Figure 1:
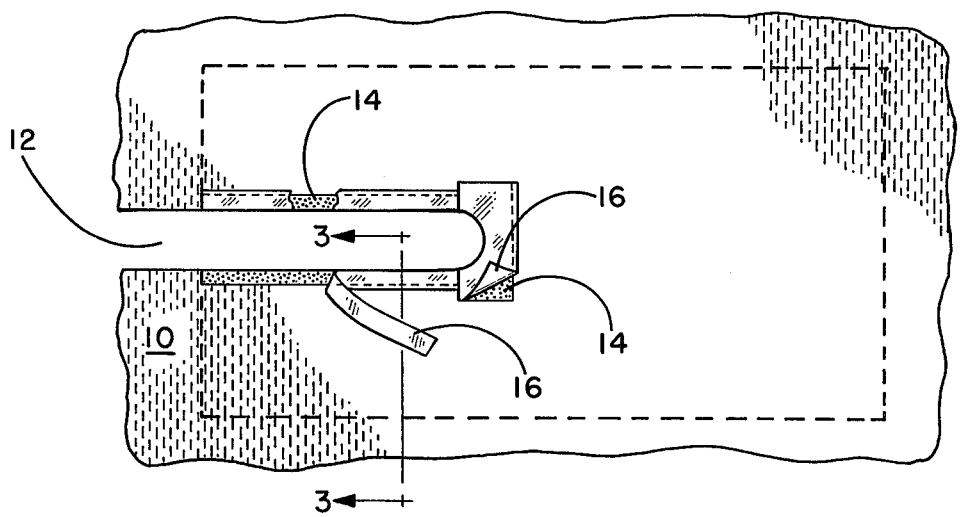
FIG. 1 is a bottom partial plan view of the drape of the present invention showing the fenestration area of the surface to contact the patient.
Figure 2:
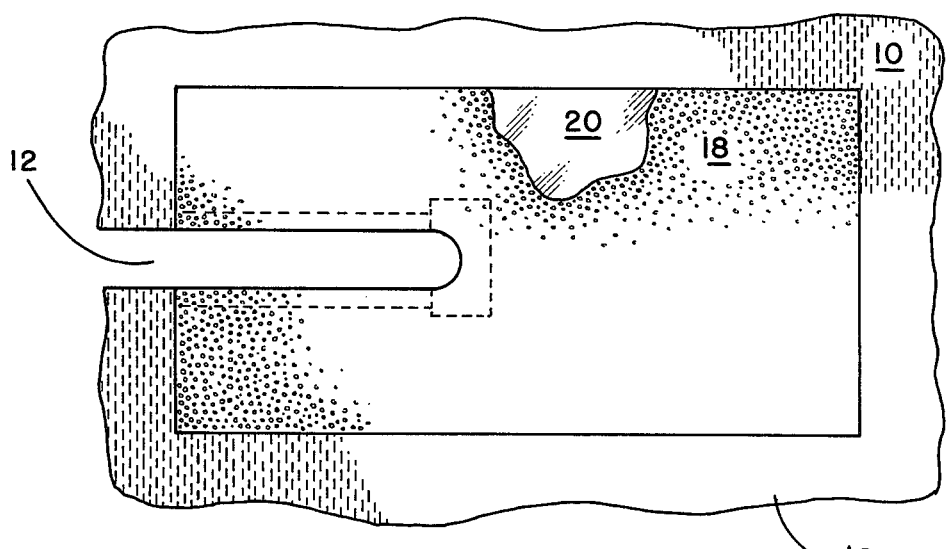
FIG. 2 is a plan view of the opposite top surface of the fenestration area of the drape of FIG. 1.
Figure 3:
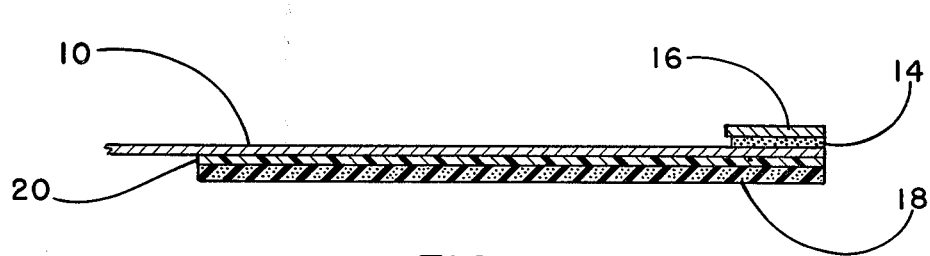
FIG. 3 is a cross-section of the drape of FIG. 1 taken along lines 3—3.
Figure 4:
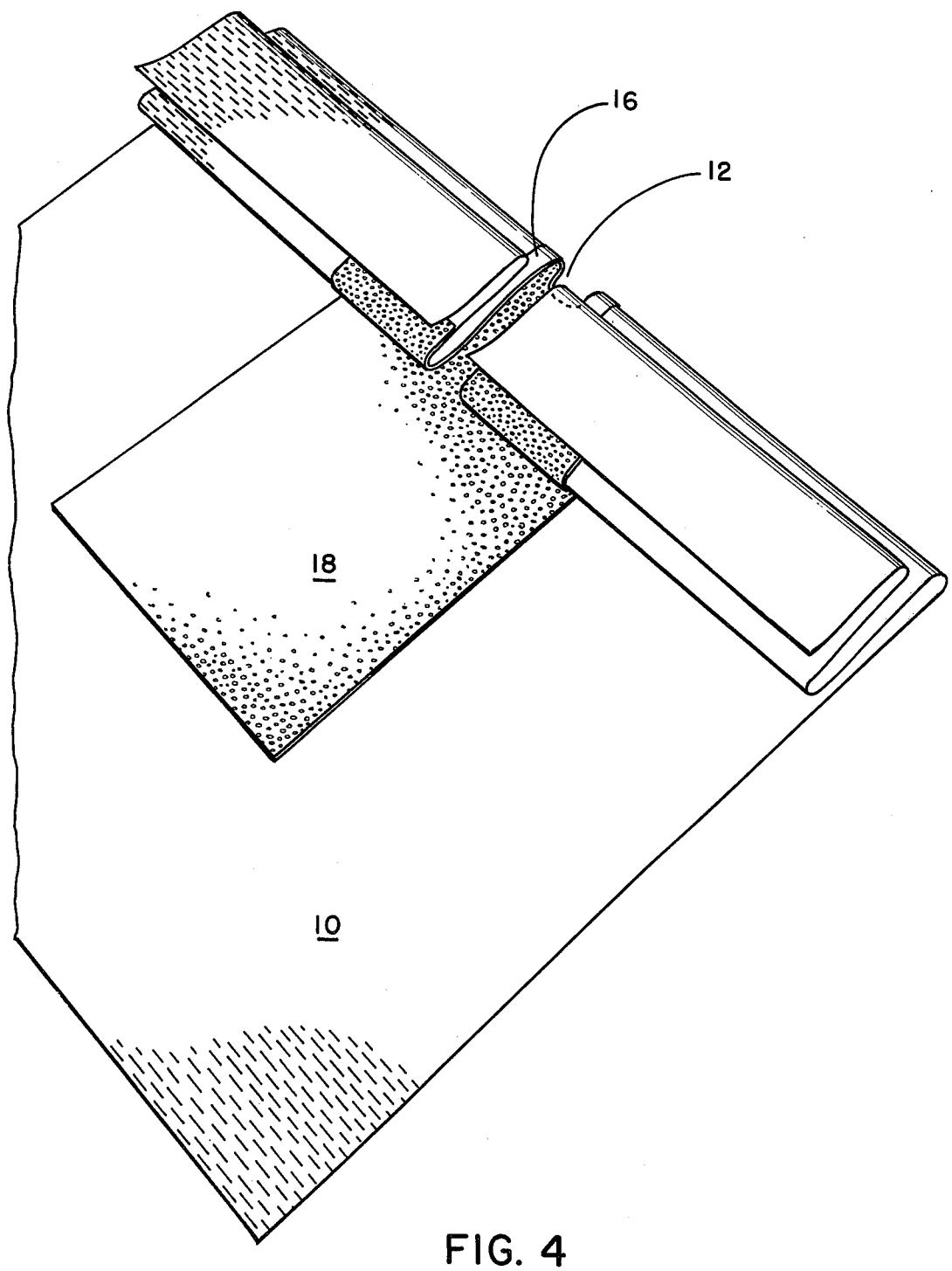
FIGS. 4–7 illustrate the method of folding the drape of the present invention.
Figure 5:
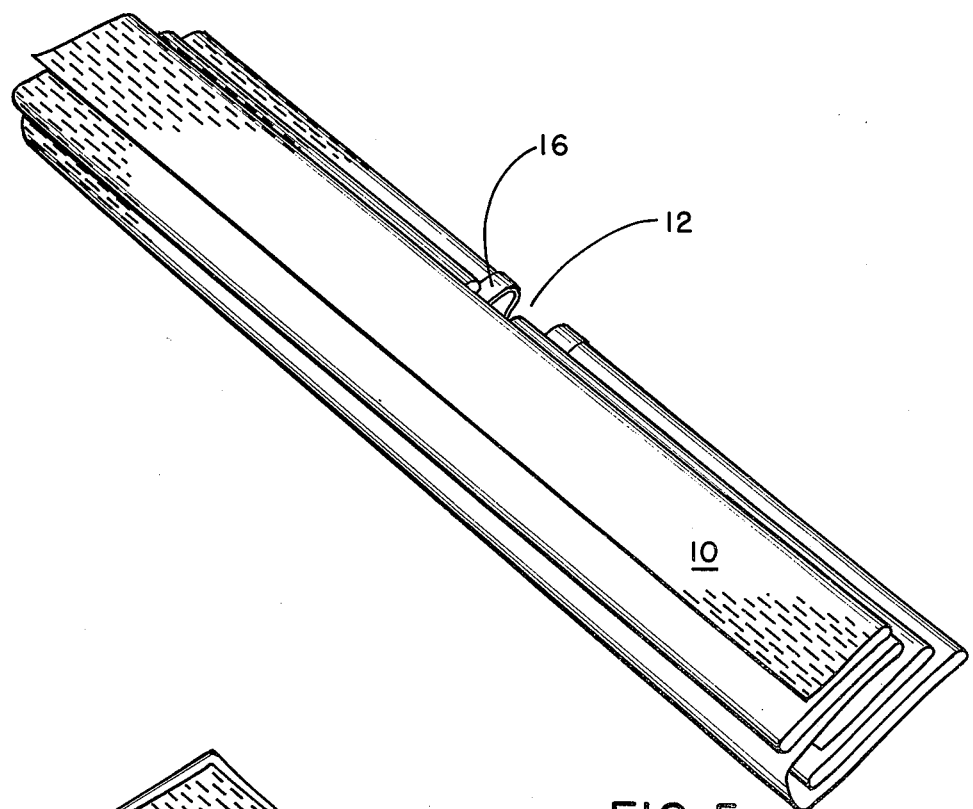

Turning to FIGS. 1–3, the embodiment illustrated therein will now be described in detail. As shown, the drape of the invention includes a base sheet 10 which is formed from a liquid-repellent material, and, for reasons of economy, preferably a nonwoven fabric. An example is a sheet formed by combining outer layers of wadding and inner layers of highly-drafted fibers disposed angularly to each other. A spaced pattern of adhesive is disposed between each fiber layer and its adjacent wadding layer with the fibers in each fiber layer partially embedded in and held by the adhesive of its adjacent adhesive layer and partially embedded in and held by the adhesive in the other adhesive layer where it extends between the fibers of its adjacent fiber layer and with a portion of the adhesive in both adhesive layers joined where the adhesive patterns are superimposed. This material is described in more detail in Sokolowski et al U.S. Pat. No. 3,484,330, issued Dec. 16, 1969, assigned to the assignee of the present invention. Other nonwoven materials, of course, may be used including scrim reinforced tissue products available under the trademark KAYCEL from Kimberly-Clark Corporation as well as random fiber reinforced tissue laminates.

At one end of base sheet 10 a portion is cut out forming U-shaped fenestration 12. The size and configuration of the fenestration will depend upon the surgical procedures for which the drape is designed, but, generally, it should be at least large enough to provide for an opening of a size to accomodate the incision when the drape is in a sealed condition. For most procedures this size will be, illustratively, within the range of from about 2 inches to 6 inches in width and 20 inches to 60 inches in length. Surrounding the fenestration 12 for at least a portion of its length and at its closed end is adhesive layer 14 which may be T-shaped and preferably is continuous for increased strength in the fenestration area. It is important that this adhesive layer surround the closed end of the fenestration and extend at least about 10 inches and preferably half the distance to the open end of the fenestration. The amount of adhesive required will depend to some extent upon the particular adhesive chosen. However, to maintain the desired sealed condition during a prolonged or complicated operative procedure, it is preferred that the adhesive layer extend about ½ to 1 inch on either side of the fenestration and that the adhesive running orthogonal to the closed end of the fenestration cover an area of about 12 square inches disposed symmetrically at the closed end of the fenestration since this area is frequently subjected to increased stress.

Normally tacky and pressure-sensitive adhesives for use herewith may be any of the biologically acceptable pressure-sensitive adhesives available. Adhesives of this class are generally composed of a film-forming elastomeric material, typically a natural or synthetic rubber, and some type of resin or other material to impart the desired degree of tack, wetting power, and specific adhesion. Typical resins include the rosin derivatives such as hydrogenated or dehydrogenated rosin or their esters. Various fillers, plasticizers, sterilizing agents, or other modifiers may also be used. For further description of such adhesives, see Kirk/Othmer, "Encyclopedia of Chemical Technology", Second Edition, Volume I, Page 382 (Interscience 1963).

Covering the adhesive layer 14 and shown partially removed for purposes of illustration only, are release strips 16. Although the release covering for the adhesive portions along the sides of fenestration 12 may be formed from either a single or multiple strips, it is essential that the adhesive portion extending from the end of the fenestration by covered by a separate release strip or portion thereof that may be removed without removing the remaining release cover portions. Preferably the release strips 16 are slightly larger than the adhesive areas being covered so as to provide a portion thereof which may be easily gripped for quick removal. The release strips 16 are, illustratively, a plastic, heavy paper or nonwoven fabric having a release coating to which the adhesive only lightly adheres. Coatings suitable for this purpose include natural or synthetic waxes, metal salts of fatty acids, polymeric materials such as polyethylene or silicone polymers, for example. Release coatings are discussed in Kirk/Othmer's "Encyclopedia", Second Edition, Vol. I, Page 1, et seq.

As illustrated, the drape of the present invention preferably includes layer 18 of a film-foam laminate on its upper surface surrounding the fenestration. The foam-film laminate is desirably of the type described in U.S. Pat. No. 3,669,106 to Schrading and Winters, issued June 13, 1972, and assigned to the assignee of the present invention. Briefly, it may include a film such as two mil anti-static polyethylene manufactures by Clopay Film Corp., anti-static polypropylene, for example "EXTREL II" available from Extrudo Film Corp., polyethylene methyl acrylate copolymer film manufactured by Edison Plastics Company, and vinyl chloride films bonded to the fibrous base sheet 10 by any suitable means such as by means of an adhesive or by extruding the film directly on the base sheet 10. The film 20 provides a fluid-impervious barrier on the top of the operative area of the base sheet 10 so that any fluids which contact this area cannot strike through the sheet. It also prevents the transfer of bacteria through the sheet to help insure sterile conditions in the operative area. The film must be capable of remaining stable under the conditions encountered in the particular treatment to which the drape is subjected to render it sterile, for example, temperatures of about 270°F for steam sterilization or about 160°F for sterilization by means of ethylene oxide or the like.

To provide a fluid-absorbent outer surface on the drape while at the same time providing a high frictional coefficient, a sheet of fluid-absorbent flexible plastic foam material 18 is desirably laminated to the outer surface of the fluid-impervious film 20. The foam material 18 may be bonded to the film 20 by any suitable means such as by means of an adhesive, by fusing, or by extruding the film 20 directly on the foam material 12. Examples of suitable foams are 40 mil polyester polyurethane foam available from Reeves Bros. Tenneco Chemicals, Inc. having a density of 1.75 pounds per cubic foot and polyether polyurethane foams. The foam thickness should be generally in the range of from about 25 mils to about 100 mils. It is preferred that the adhesive layer and the foam-film laminates be coextensive on opposite surfaces of the base sheet. Further, the adhesive layer and the release liner preferably do not extend by any amount into the fenestration area, but are separated from the fenestration edge by up to about 1/16 inch.

Figure 6:
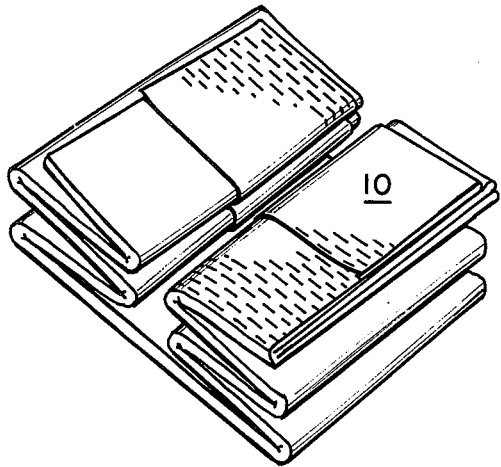
Figure 7:
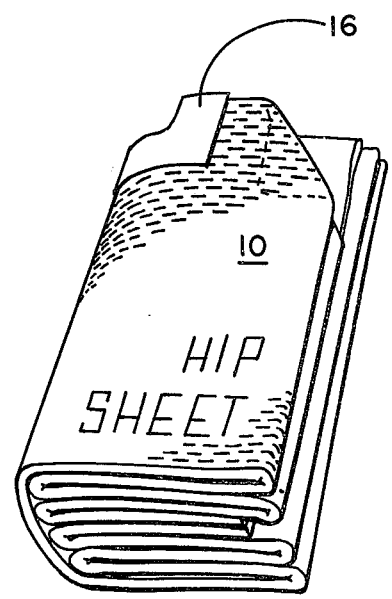
Figure 8A:
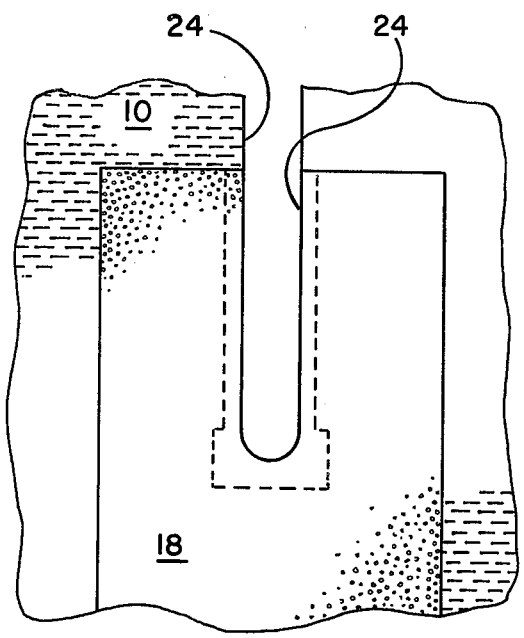
FIG. 8 illustrates variations in fenestration size and configuration obtainable with the drape of the present invention.
Figure 8B:
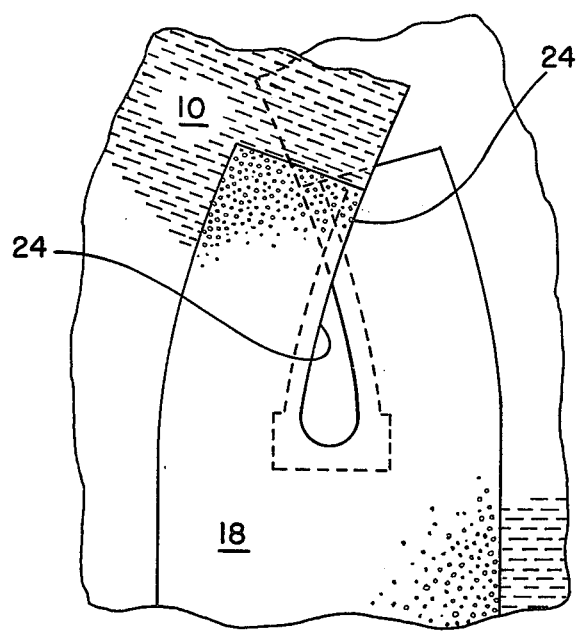
Figure 8C:
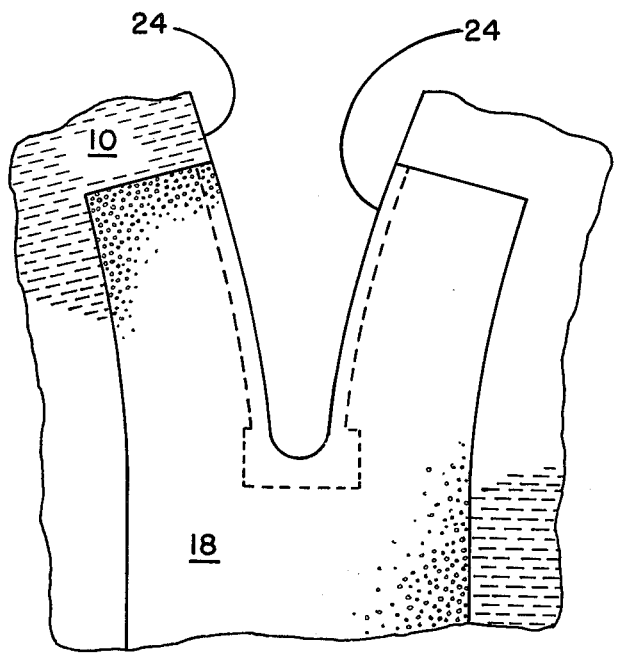
Figure 8D:
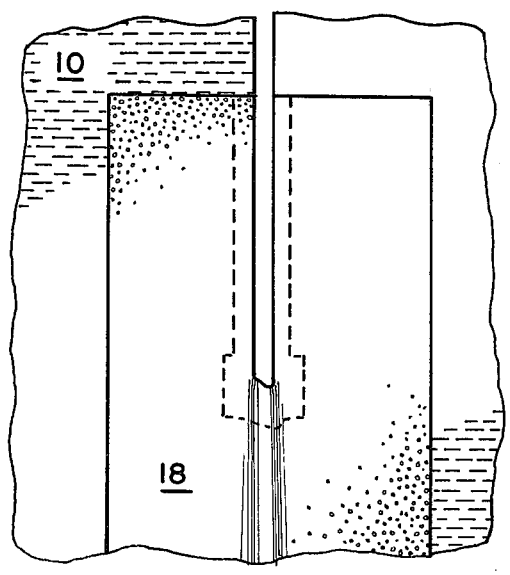

Turning to FIGS. 4–7, the preferred folding method for the drape of the invention will be described. As illustrated, the drape is first fan-folded starting at the fenestration end. In order to reduce the risk of contamination from the patient's skin when unfolding, each fold is made slightly larger than the preceding fold so that the smallest fold is on the top and each successive fold extends laterally by about 1 to 2 inches. Next, the opposite end is brought over the top of the fan-folded portion and itself fan-folded so as to present three fan-folded portions in vertical cross-section, the uppermost being shortened to provide a gripping edge. Then this folded drape is fan-folded laterally depending upon the length of the stack as shown in FIG. 6 so as to provide equal fan-folded edges on a base of 12–18 inches, for example. Finally, as shown in FIG. 7, one corner is "dog-eared" or folded over so that the center of the folded drape may be quickly located, and the fold folded in half with descriptive information stamped so as to be immediately legible when the drape is unwrapped.

FIG. 8 illustrates in fragmentary views the variable fenestration dimensions obtainable with the drape of the invention. By adjusting the position of tails 24 an open or nearly closed fenestration may be obtained. FIG. 8a shows the drape in a flat, open fenestration configuration as it would be normally unfolded. FIG. 8b demonstrates a closed fenestration of reduced size obtained by crossing tails 24 and attaching them by the underside adhesive layer. FIG. 8c depicts a larger fenestration provided by spreading tails 24 apart, and FIG. 8d depicts a narrow fenestration resulting from placing tails 24 closer together. In all cases a substantially complete seal around the fenestration can be maintained when used in combination with an adhesive bar sheet, or, in the case of FIG. 8b, without the need for an additional sheet.

Figure 9:
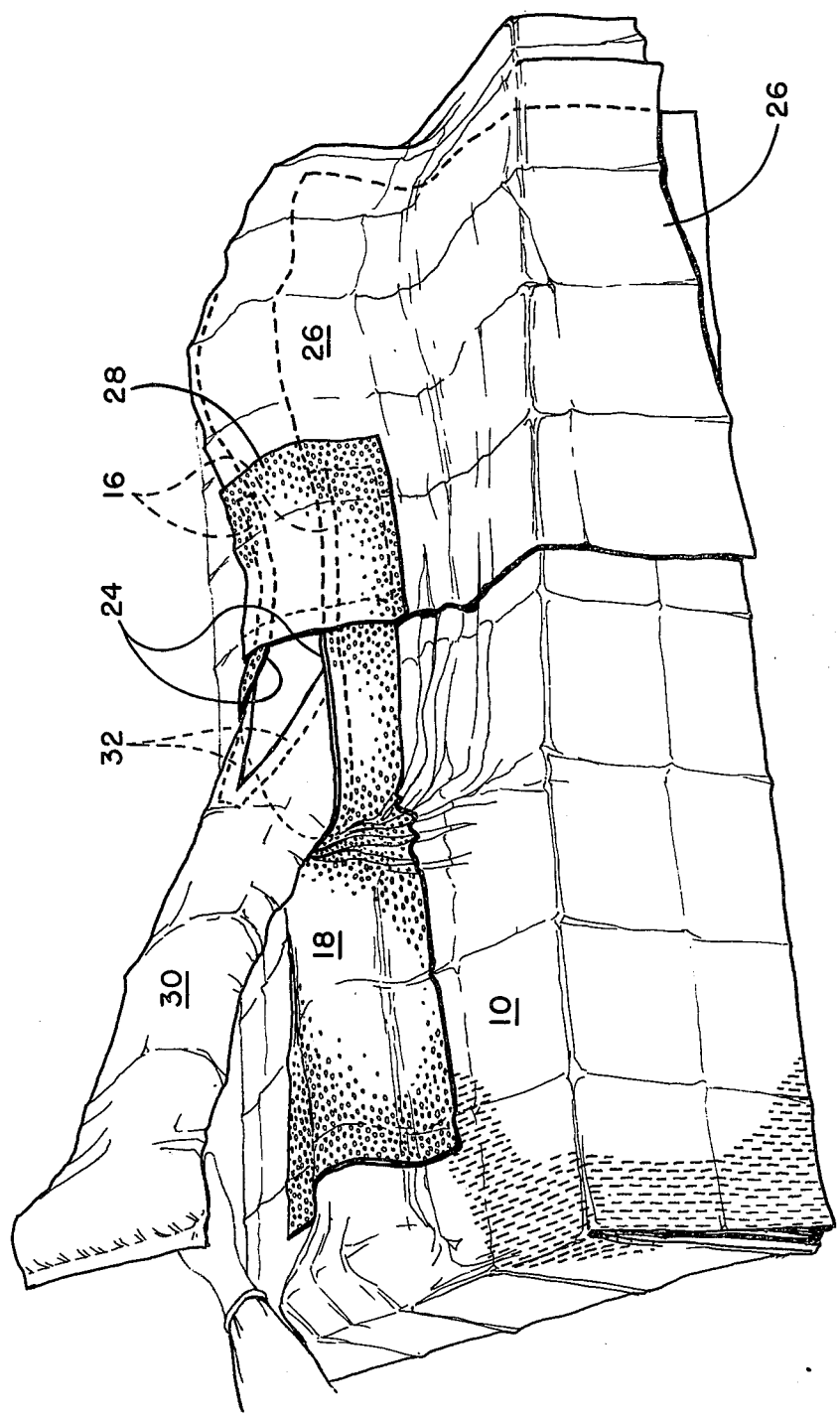
FIG. 9 illustrates the drape of the present invention in use.

Turning to FIG. 9, the drape of the present invention in use in a complex operative procedure involving a patient's hip will be described. In use the last fold of the above-mentioned folding procedure is unfolded so that the closed end of the fenestration with its adhesive and release liner are exposed. The liner is then removed by peeling away from the body to avoid contact, and that adhesive portion positioned in the perineal area and sealed against the patient. Thus positioned, the drape may be easily unfolded and will maintain its correct position. When this is done, the two tails of the fenestration may then be brought alongside the patient's torso, the release sheets removed by peeling away from the body, and the tails positioned so as to seal off the sides of the operative field. Alternatively, the tails 24 may be crossed at the level of the patient's waist and sealed forming an operative field as in FIG. 8b that completely seals off the patient's hip from the remainder of his body. As illustrated, bar sheet 26 having a film-foam laminate area 28 may be utilized in combination with the drape of the present invention to cover exposed patient areas and stocking 30 may also be provided for complete draping. In the manner shown, stocking 30 preferably has underside adhesive portions 32 which combines with the drape and bar sheet 26 to seal completely around the fenestration. As illustrated and described, the drape of the present invention provides an integral part of a total draping system and allows for increased speed in draping and security in the draping and operative procedures.

Thus it is apparent that there has been provided in accordance with the invention a surgical drape that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:
1. Surgical drape comprising
   a. a base sheet formed of liquid repellent nonwoven fabric material, said base sheet having a top surface and a bottom surface for contacting a patient and having a generally U-shaped fenestration along a portion thereof to form tails;
   b. a continuous layer of normally tacky pressure-sensitive adhesive on the bottom of said base sheet adjacent the closed end of said U-shaped fenestration; and extending adjacent the fenestration sides at least half way to the opened end of said fenestration;
   c. releasable cover means protecting said adhesive adjacent the sides of said fenestration; and
   d. separate releasable cover means protecting said adhesive at the closed end of said fenestration,
      said drape being folded so that said separate releasable cover means protecting the adhesive at the closed of said fenestration is exposed.
2. The drape of claim 1 further including a foam-film laminate bonded to the top surface of said base sheet and providing an absorbent, low glare, frictional surface having increased resistance to liquid strikethrough.
3. The drape of claim 1 in combination with a stocking drape and a bar drape forming a draping system for complicated limb surgery.
4. The drape of claim 1 wherein said adhesive layer covers an area of at least about 12 square inches disposed symmetrically at the closed end of the fenestration.
5. The drape of claim 1 wherein said base sheet is a nonwoven laminate of wadding and highly drafted fibers bonded by a spaced pattern of adhesive.
6. The drape of claim 1 wherein said base sheet is a random fiber reinforced tissue laminate.
7. The drape of claim 1 wherein said base sheet is a scrim reinforced tissue material.
8. The drape of claim 1 wherein said releasable cover means are larger than the area of said adhesive so as to provide for quick cover removal.
9. The drape of claim 2 wherein the areas of adhesive and foam-film laminate are coextensive on opposite sides of said base sheet.
10. The drape of claim 1 wherein said adhesive layer and releasable cover means do not extend into the fenestration and are separated from the fenestration edge by up to about 1/16 inch.

* * * * *

UNITED STATES PATENT OFFICE
CERTIFICATE OF CORRECTION

PATENT NO. : 3,930,497

DATED : January 6, 1976

INVENTOR(S) : Kay E. Krebs and Marion T. Arps

It is certified that error appears in the above-identified patent and that said Letters Patent are hereby corrected as shown below:

Column 4, line 23, "manufactures" should read -- manufactured --.
Column 6, claim 1, last line, "closed of" should read -- closed end of --.

Signed and Sealed this

Twenty-seventh Day of April 1976

[SEAL]

Attest:

RUTH C. MASON
Attesting Officer

C. MARSHALL DANN
Commissioner of Patents and Trademarks